United States Patent
Park (10) Patent No.: US 9,993,388 B2
(45) Date of Patent: Jun. 12, 2018

(54) FOOTWEAR-TYPE GROWTH STIMULATION APPARATUS

(71) Applicant: Sjay Medience Co., Ltd., Seoul (KR)

(72) Inventor: Ki Won Park, Seoul (KR)

(73) Assignee: SJAY MEDIENCE CO., LTD., Seoul (KR)

(*) Notice: Subject to any disclaimer, the term of this patent is extended or adjusted under 35 U.S.C. 154(b) by 46 days.

(21) Appl. No.: 15/102,027

(22) PCT Filed: Dec. 27, 2013

(86) PCT No.: PCT/KR2013/012235
§ 371 (c)(1),
(2) Date: Jun. 6, 2016

(87) PCT Pub. No.: WO2015/083879
PCT Pub. Date: Jun. 11, 2015

(65) Prior Publication Data
US 2016/0310360 A1     Oct. 27, 2016

(30) Foreign Application Priority Data
Dec. 6, 2013  (KR) ................. 10-2013-0151247

(51) Int. Cl.
*A61H 39/00* (2006.01)
*A43B 3/00* (2006.01)
(Continued)

(52) U.S. Cl.
CPC ......... *A61H 39/002* (2013.01); *A43B 3/0005* (2013.01); *A43B 3/12* (2013.01);
(Continued)

(58) Field of Classification Search
CPC ................. A61H 39/002; A61H 39/04; A61H 2201/0165; A61H 2201/10;
(Continued)

(56) References Cited

U.S. PATENT DOCUMENTS

2006/0235465 A1* 10/2006 Koo ................. A43B 1/0054
606/204
2009/0149899 A1* 6/2009 Ahn ................. A43B 3/0005
607/3

FOREIGN PATENT DOCUMENTS

JP          3111460 U      6/2005
KR       10-0375880 B1     3/2003
(Continued)

OTHER PUBLICATIONS

International Search Report issued for International Application No. PCT/KR2013/012235 dated Sep. 1, 2014 (2 pages).
(Continued)

*Primary Examiner* — Carl H Layno
*Assistant Examiner* — Erin M Piateski
(74) *Attorney, Agent, or Firm* — Rothwell, Figg, Ernst & Manbeck, P.C.

(57) ABSTRACT

The present invention relates to a footwear-type growth stimulation apparatus, and more specifically to a growth stimulation apparatus which can give a low-frequency stimulus to a front portion of the sole of the foot of a user who wears it on his/her feet during sleep, can give a continuous stimulus by preventing the feet from being removed therefrom due to twisting and turning during sleep, and can promote the secretion of growth hormone by allowing the weight to be concentrated on the front portion of the sole of the foot even during walking and thus performing continuous Bubbling Spring acupressure.

4 Claims, 4 Drawing Sheets

(51) Int. Cl.
  *A43B 3/12* (2006.01)
  *A43B 7/14* (2006.01)
  *A61N 1/32* (2006.01)
  *A61N 1/36* (2006.01)
  *A61H 39/04* (2006.01)
  *A43B 7/00* (2006.01)
  *A61N 1/04* (2006.01)

(52) U.S. Cl.
  CPC .............. *A43B 3/126* (2013.01); *A43B 3/128* (2013.01); *A43B 7/00* (2013.01); *A43B 7/145* (2013.01); *A43B 7/146* (2013.01); *A43B 7/1445* (2013.01); *A61H 39/04* (2013.01); *A61N 1/0484* (2013.01); *A61N 1/326* (2013.01); *A61N 1/36014* (2013.01); *A61H 2201/0165* (2013.01); *A61H 2201/10* (2013.01); *A61H 2201/164* (2013.01); *A61H 2201/165* (2013.01); *A61H 2201/5033* (2013.01); *A61H 2201/5043* (2013.01); *A61H 2205/12* (2013.01); *A61H 2205/125* (2013.01); *A61N 1/0492* (2013.01)

(58) Field of Classification Search
  CPC .......... A61H 2201/164; A61H 2201/16; A43B 3/0005; A43B 3/12; A43B 3/126; A43B 3/128; A43B 7/00; A43B 7/1445; A43B 7/145; A43B 7/146; A61N 1/0484; A61N 1/326; A61N 1/36014
  USPC ........................................................ 607/144
  See application file for complete search history.

(56) References Cited

FOREIGN PATENT DOCUMENTS

| KR | 20-0409793 Y1 | 3/2006 |
| KR | 20-0411462 Y1 | 3/2006 |
| KR | 10-0669125 B1 | 1/2007 |
| KR | 20-2013-0001116 U | 2/2013 |

OTHER PUBLICATIONS

Office Action issued for Japanese Patent Application No. 2016-536902 dated Apr. 18, 2017, with English translation (6 pages).

* cited by examiner

FOOTWEAR-TYPE GROWTH STIMULATION APPARATUS

CROSS-REFERENCE TO RELATED APPLICATIONS

This application is a 35 U.S.C. § 371 National Phase Entry Application from PCT/KR2013/012235, filed on Dec. 27, 2013, and designating the United States, which claims priority under 35 U.S.C. § 119 to Korean Patent Application No. 10-2013-0151247, filed on Dec. 6, 2013, the entire contents of which are incorporated herein by reference.

TECHNICAL FIELD

The present invention relates to a footwear-type of growth stimulation apparatus, and more particularly, to a growth stimulation apparatus that: may be worn on the feet in order to thereby provide a low-frequency stimulus to the front portion of the soles of a user's feet while asleep; may be prevented from being detached from the feet due to twisting and turning while asleep in order to thereby provide continuous stimulus; and may allow the user's weight to be concentrated on the front portion of the soles of the user's feet even while walking in order to thereby promote the secretion of growth hormones by providing continuous Bubbling Spring acupressure.

BACKGROUND ART

Studies have shown that the height of people is affected by congenital factors by 23% and acquired factors by 77%, respectively. Here, the congenital factors are unchangeable, whereas the acquired factors are controllable. Therefore, the careful management of the parent is required in order for the children to become tall.

Meanwhile, there are many kinds of hormones that are secreted in the human body, which have a lot of functions. Hormones regulate the biological rhythms for 24 hours, and are closely related to homeostasis of the body, such as, body water regulation, food intake and metabolism, reproduction, immunity, or production of red blood cells. Thus, even a small imbalance of the hormones may interfere with health. Among them, growth hormones, which play an important role for height growth, are one of the most particular hormones, and serve to create growth factors in the liver in order to thereby accelerate the metabolism in the body. Since the secretion of the growth hormones is susceptible to physical conditions, such as nutrition, exercise, or sleep, it is necessary to maintain good conditions to facilitate the secretion of the grow hormones. In particular, a deep sleep brings about more secretion of the growth hormones. Sleep is about relaxation and energy, and is essential to the height growth.

For example, the brain shows brain waves in a specific pattern during sleep. The brain waveform shows that an REM sleep state and a non-REM sleep state are repeated. The REM sleep refers to a state of light sleep in which the eyes randomly move in sleep, and the non-REM sleep refers to a state of deep sleep without the movement of the eyes. It has been known that the secretion of the growth hormones increases in the non-REM sleep state, in which a sleeper falls into a deep sleep and does not wake up easily at noises, among the sleep states above.

Therefore, it is necessary to continuously transfer stimulus through growth stimulation points in the non-REM sleep state in order to thereby promote the secretion of the growth hormones.

Korean Utility Model Registration No. 20-0468997 (registered on 5 Sep. 2013, referred to as "Reference 1") "Foot Instrument for Growth Stimulator", which has been invented by the present inventor, suggests a foot instrument that has stimulation pads that are formed on four portions, such as the Bubbling Spring in the middle of the front portion of the sole, a portion where a big toe is joined in the front portion of the sole, a portion where a little toe is joined in the front portion of the sole, and a portion under the big toe. The foot instrument of Reference 1 adopts a fastener that has Velcro bands as a means for biasing the contact surface, on which the stimulation pads are formed, to the sole. However, since the foot instrument is fastened only around the top of the foot, the foot instrument may be detached from the foot due to twisting and turning while asleep.

Korean Patent Publication No. 10-2011-0056613 (published on 31 May 2011, referred to as "Reference 2") "Build Growth Palpation or Health Energy Chip Sticking Band" discloses a highly elastic band that is worn on the ankle and has energy chips embedded in the portion of the ankle in order to thereby press the ankle by the energy chips for stimulation. The ankle is stimulated by the volume of the embedded energy chips in Reference 2, but Reference 2 does not show the details of the provided energy, and the energy is merely estimated to be far-infrared radiation. Therefore, it cannot provide the effect of a low-frequency wave.

Korean Patent Publication No. 10-2000-0051458 (published on 8 Mar. 2002, referred to as "Reference 3") "Shoes having Low Frequency Massage Function" is intended to perform a foot massage by arranging a plurality of patches on the top surface of an insole and generating low frequency waves through a remote controller when it is needed. However, since the shoes of Reference 3 are existing commercial shoes, the user cannot wear the same while sleeping at home.

DETAILED DESCRIPTION OF THE INVENTION

Technical Problem

Therefore, a growth stimulation apparatus of the present invention has the object to provide an apparatus
that gives a low frequency stimulus to the front portion of the sole of the foot while asleep in order to thereby promote the secretion of growth hormones, and prevents the apparatus from being detached due to twisting and turning in order to thereby continue to provide a low frequency stimulus.

In addition, the object of the present invention is to continue to provide acupressure by stimulation pads that are formed on the top surface of a bottom body of a growth stimulation apparatus by concentrating the weight on the front portion of the sole of the foot while walking with the increase in the thickness of a cushion while forming only the front portion of the bottom body of the growth stimulation apparatus.

Technical Solution

In order to solve the objects above, a growth stimulation apparatus of the invention may include: a main body configured to have an outer sheath layer on which a contact surface is formed to come into contact with only the front portion of a sole and that has a plurality of stimulation pads formed on the contact surface, and a cushion layer that is integrally coupled with the lower surface of the outer sheath layer to provide a cushion and that has a receptacle formed on one side thereof to have a connected terminal to be connected with a plurality of stimulation pads by electric cables; a control box configured to be detachably mounted in the receptacle of the main body and configured to have a battery room and a control room that are provided therein to generate low frequency waves by using supplied power and to then transfer the generated low frequency waves to the stimulation pads through the connected terminal of the receptacle; an upper cover configured to be extended from both ends of the top surface of the main body to wrap the top of a foot; and a hooking band configured to be integrally coupled to the upper cover to be extended backwards and configured to be formed of an elastic material to be hooked by the heel of the foot.

An on-off switch may be installed on the outer surface of the control box for operation, and a rest period operation and a stimulation period operation are repeatedly performed when the switch is in the on mode.

In addition, the stimulation pads may be formed on four portions of the outer sheath layer, such as the Bubbling Spring in the middle of the front portion of the sole, a portion where a big toe is joined in the front portion of the sole, a portion where a little toe is joined in the front portion of the sole, and a portion that comes into contact with the lower surface of the big toe, and acupressure protrusions may be formed on the stimulation pads to provide acupressure to the sole.

In addition, the hooking band may include: a bottom support configured to be extended downwards and slantingly from the back of the upper cover to wrap the back portion of the sole; and a back support configured to be extended backwards from one side of the bottom support to wrap the upper portion of the heel.

Advantageous Effects

The growth stimulation apparatus of the present invention, according to the technical solution above,
has a hooking band for preventing the apparatus from being attached even if the wearer twists and turns while asleep in order to thereby maintain the contact between the stimulation pads and the soles and in order to thereby transfer low frequency waves, which are generated by a control box, to the body as much as possible for a configured period of time so that the secretion of growth hormones can be maximized.

In addition, when the growth stimulation apparatus is worn, the heels of the feet are spaced a specific distance from the floor in order to thereby allow the wearer to walk while lifting up the heels so that the weight can be concentrated on the front portion of the soles of the feet. At this time, the stimulation pads, which are positioned in the front portion of the soles of the feet, on which the weight is concentrated, have acupressure protrusions formed thereon in order to thereby provide stimulus by acupressure without operating the control box and in order to thereby promote the secretion of the hormones.

DESCRIPTION OF REFERENCE NUMERALS

10: Growth stimulation apparatus
20: Main body
21: Outer sheath layer, 22: Cushion layer
23: Stimulation pads, 24: Electric wires
25: Connected terminal, 26: Receptacle
27: Slide prevention bump
221: Electric wire burial groove, 231 to 234: First to Fourth Stimulation Pads
235: Acupressure protrusion, 236: Electric wire connection groove
30: Control box
31: Box body, 32: Battery room
33: Low frequency wave generating room, 34: Connecting terminal
35: On-off switch, 36: Light display unit
331: Low frequency wave generator
40: Upper cover
41: First cover portion, 42: Second cover portion
43: Tightening member, 44: Auxiliary cover portion
45: Auxiliary cover band
50: Hooking band
51: Bottom support, 52: Back support

MODE FOR CARRYING OUT THE INVENTION

Hereinafter, the present invention will be described in more detail with reference to the accompanying drawings.

Figure 1:
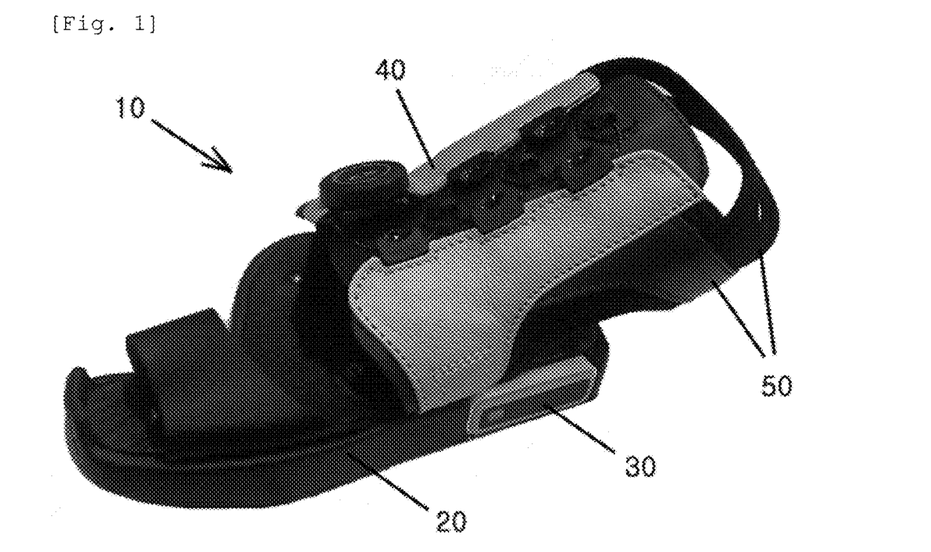
FIG. 1 is a perspective picture showing the footwear-type of growth stimulation apparatus, according to the embodiment of the present invention.
Figure 2A:
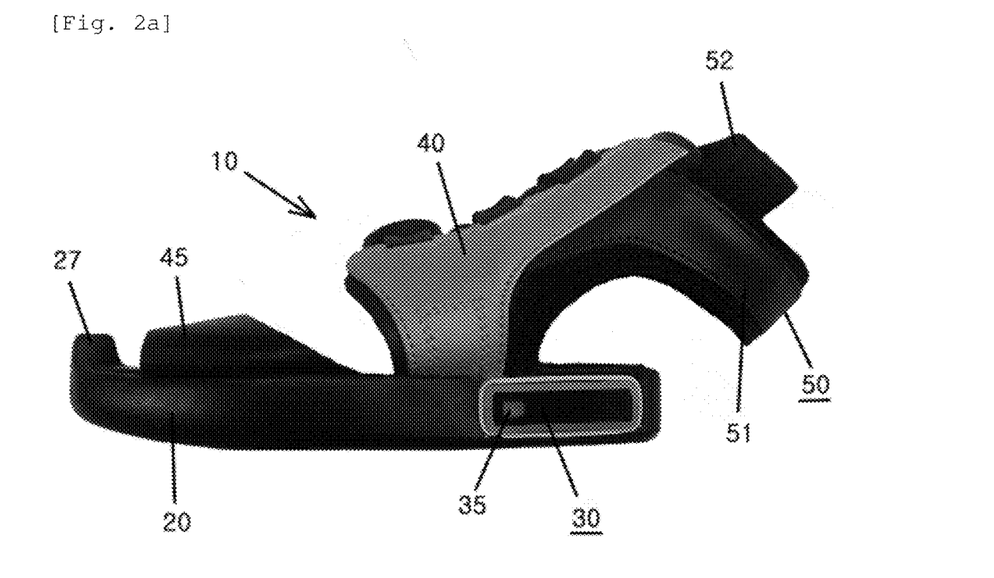
FIGS. 2a and 2b are a side picture showing the footwear-type of growth stimulation apparatus and an exemplary view of wearing the same, according to the present invention, respectively.
Figure 2B:
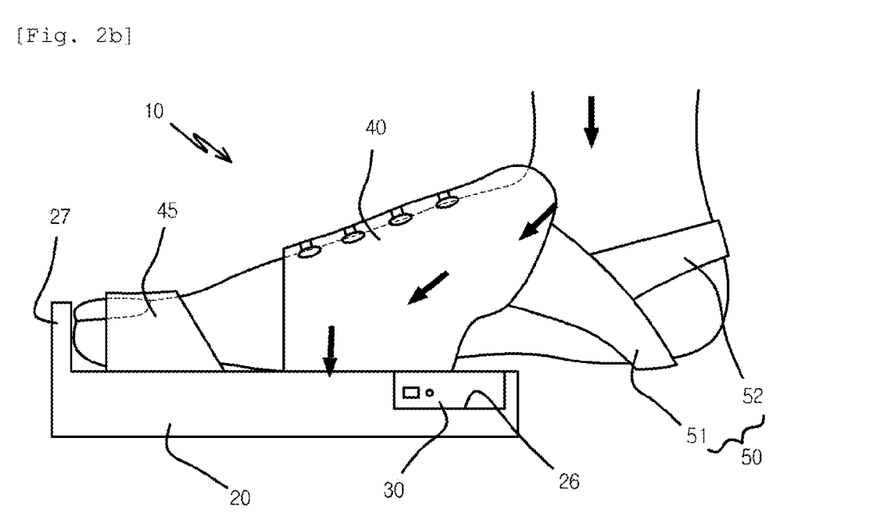
Figure 3:
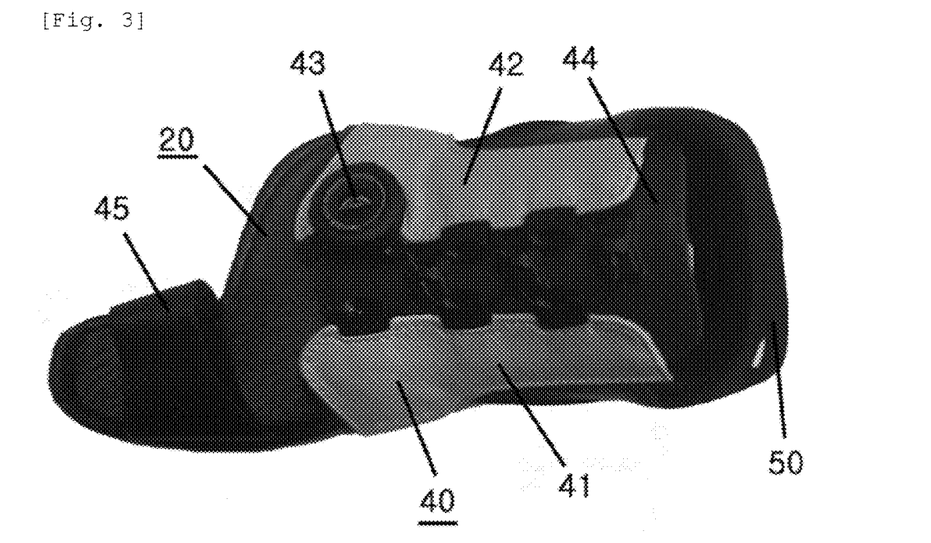
FIG. 3 is a plan picture showing the footwear-type of growth stimulation apparatus, according to the present invention.
Figure 4A:
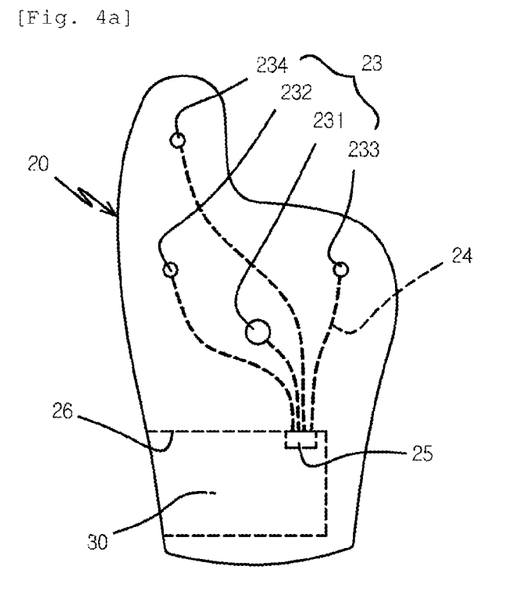
FIGS. 4a and 4b are a plan view and a sectional view illustrating a main body of the footwear-type of growth stimulation apparatus, according to the present invention.
Figure 4B:
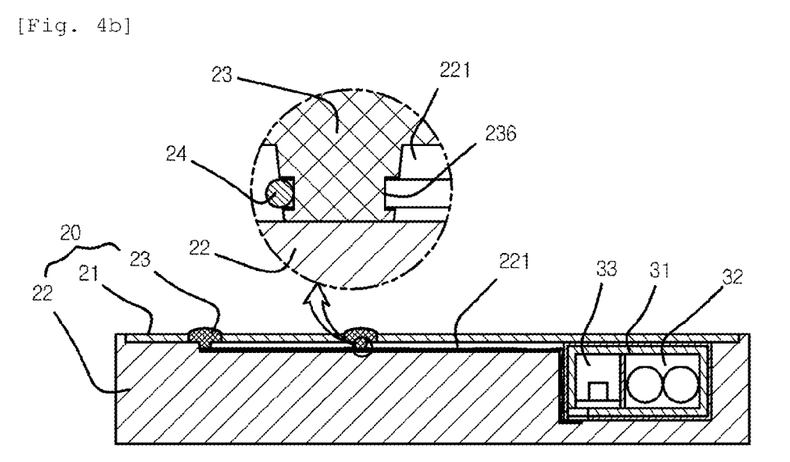
Figure 4C:
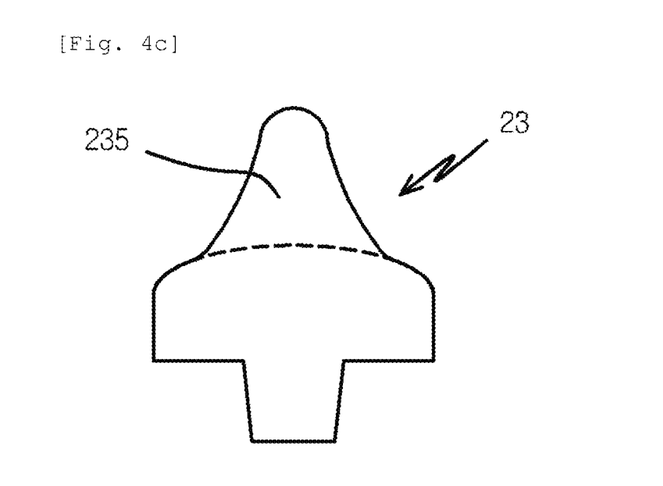
FIG. 4c is a sectional view illustrating another embodiment of a stimulation pad, according to the present invention.
Figure 5:
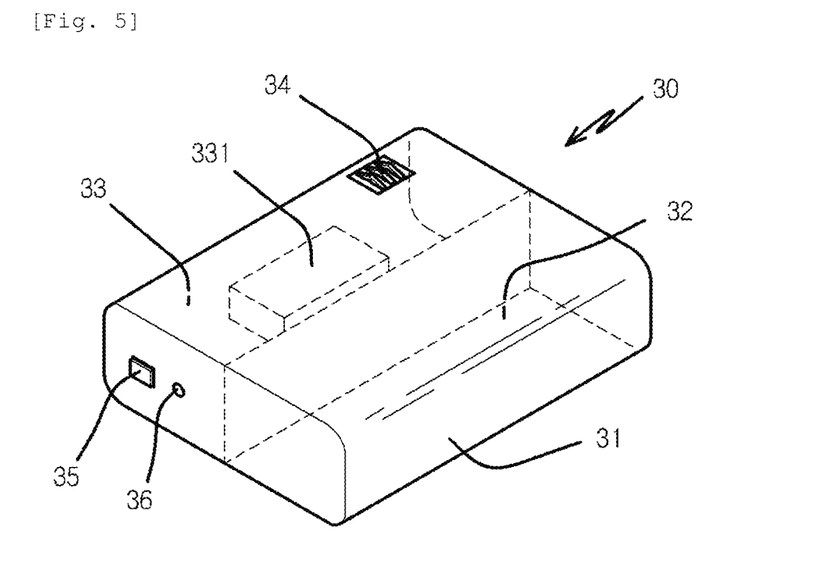
FIG. 5 is a perspective view illustrating a control box of the footwear-type of growth stimulation apparatus, according to the present invention.

FIG. 1 is a perspective picture showing the footwear-type of growth stimulation apparatus, according to the embodiment of the present invention, and FIGS. 2a and 2b are a side picture showing the footwear-type of growth stimulation apparatus and an exemplary view of wearing the same, according to the present invention. FIG. 3 is a plan picture showing the footwear-type of growth stimulation apparatus, according to the present invention, and FIGS. 4a and 4b are a plan view and a sectional view illustrating a body of the footwear-type of growth stimulation apparatus, according to the present invention. FIG. 5 is a perspective view illustrating a control box of the footwear-type of growth stimulation apparatus, according to the present invention, and FIG. 4c is a sectional view illustrating another embodiment of a stimulation pad, according to the present invention.

The footwear-type of growth stimulation apparatus 10, according to the present invention, is provided as a pair of left and right apparatuses that are symmetrical, and the description and the drawings will be mainly made of a right growth stimulation apparatus in the present invention.

The growth stimulation apparatus 10 is configured to include: a main body 20 that constitutes the bottom in the form of a shoe; a control box 30 that is detachably coupled to the body; an upper cover 40 that covers the upper portion of the body; and a hooking band 50 that is extended from the rear portion of the upper cover.

First, the main body 20 is formed to have a specific thickness similar to that of the bottoms of general shoes. However, the main body 20 is provided in the form that comes into contact only with a front portion including toes among the soles of the user's feet as shown in the drawing. The main body 20 is formed such that the rear portion thereof, on which the heels of the feet rest, is removed, compared with the bottoms of the general shoes. The main body 20 has a length of two thirds of the bottoms of the general shoes from the front end to the rear, and has a thickness of 10 to 20 mm so that when the user wears it and stands up, the heels of the feet may be lifted up in order to thereby concentrate the user's weight on the front portion. Furthermore, toe resting portions may be formed such that remaining portions except for a big toe resting portion are removed in order to thereby concentrate the user's weight on the big toe portion when standing up. This is intended to maximize the acupressure effect by stimulation pads that will be described below. In addition, a slide prevention bump 27 is formed on the front end of the main body, on which the big toe rests, in order to thereby prevent the big toe from sliding forward on the top surface of the main body so that the big toe can rest in its position.

The main body 20 in the form above has: an outer sheath layer 21 that is formed of leather of a soft material on the contact surface that directly comes into contact with the soles of the user's feet; and a cushion layer 22 of a specific thickness is formed under the outer sheath layer 21 in order to thereby absorb shock from the bottom when standing up, as shown in FIGS. 4*a* and 4*b*.

In addition, a plurality of stimulation pads 23 are installed in the outer sheath layer 21 that is the top surface of the main body 20 as shown in FIGS. 4*a* and 4*b*. The stimulation pads 23 are formed of a conductive material though which a current is able to flow, and the top surface of the stimulation pad, which is exposed through the outer sheath layer 21, is formed to be wide in order to thereby come into contact with the soles of the user's feet. In addition, the lower surface of the stimulation pad protrudes long to pass through the outer sheath layer, and one side of the protruded portion is connected with an electric wire 24 to be applied with a current. The top surface of the stimulation pad 23 is formed to have a diameter in the range of 7 to 11 mm in order to thereby provide a sufficient contact surface with the soles of the user's feet, and a connection member, which protrudes downwards from the stimulation pad 23, may be formed to be long enough to penetrate through the cushion layer 22 and fixed therein. The member, which protrudes downwards, is formed with an annular wire connection groove 236 in order to easily wind an electric wire around the same for a connection. Furthermore, an electric wire burial groove 221 may be formed on the top surface of the cushion layer 22 so that the electric wires connected with the stimulation pads may be buried therein in order to thereby prevent the protrusion of the outer sheath layer due to the electric wires and in order to thereby improve a feeling of wearing.

In addition, the top surface of the stimulation pad 23, which comes into contact with the soles of the user's feet, may protrude upwards to form an acupressure protrusion 235 as shown in FIG. 4*c*. The acupressure protrusion 235, which protrudes upwards, is intended to press the soles for acupressure. The protruding height of the top surface of the stimulation pad may be within a range of 3 to 8 mm in order to thereby provide an acupressure effect by the user's weight when the user wears the growth stimulation apparatus and stands up. In particular, since there is no main body of the growth stimulation apparatus in the portion corresponding to the heels of the feet, the user may lift up the heels when standing up, so that the user's weight may be concentrated on the front portion of the soles in order to thereby further increase the acupressure effect.

The stimulation pads 23 may include: the first stimulation pad 231 that comes into contact with the Bubbling Spring in the middle of the front portion of the user's sole when the apparatus is worn; the second stimulation pad 232 that comes into contact with a portion where a big toe is joined in the front portion of the sole; the third stimulation pad 233 that comes into contact with a portion where a little toe is joined in the front portion of the sole; and the fourth stimulation pad 234 that comes into contact with a big toe, which are formed to be supplied with a current.

The Bubbling Spring is positioned in the center corresponding to one third of the length of the sole from the front end of the toe. According to Oriental medicine, it is known that the Bubbling Spring is related to a kidney. Thus, if the Bubbling Spring is stimulated, the kidney is also stimulated to thereby strengthen the renal function and to thereby promote the height growth. In addition, a big toe is a foot reflex point corresponding to the pituitary gland, and the secretion of growth hormones may be promoted by stimulating the same. In addition, the front portion of the sole, which is joined to the big toe, is a foot reflex point corresponding to the parathyroid gland, and the portion that is joined to the little toe is a foot reflex point corresponding to bronchial tubes and lungs. The environment to promote the secretion of growth hormones may be provided by strengthening respective foot reflex points and by then maintaining a restful sleep.

The first stimulation pad 231 may have a diameter of approximately 10 mm, and the second to fourth stimulation pads 232 to 234 may have diameters of approximately 7 mm, which may receive low frequency waves in order to thereby stimulate the human body. It is possible to maintain the balance of the human body through the current supply by applying low frequency waves that have different polarities to the first stimulation pad 231 and the second to fourth stimulation pads 232 to 234, respectively. For example, the first stimulation pad 231 is applied with a low frequency wave of a "+" polarity, and the second to fourth stimulation pads 232 to 234 are applied with a low frequency wave of a "−" polarity.

In addition, a receptacle 26 is formed on one side of the cushion layer 22 of the main body 20. The receptacle 26 may accept a control box 30, which will be described below, therein, and the inner wall of the receptacle may be formed of high strength plastic or a metallic material in order to thereby prevent the accepted control box from being pressed by an external force. The receptacle 26 having the high strength inner wall may be formed inside the cushion layer. Alternatively, the receptacle 26 having the high strength inner wall may be formed under the top surface of the cushion layer 22, and then the outer sheath layer 21 may be stacked thereon to form the main body.

In addition, a connected terminal 25, which is connected with the control box 30, is formed on the inner surface of the receptacle 26. The connected terminal 25 is connected to the first to the fourth stimulation pads 231 to 234 by electric wires 24, respectively, in order to thereby transfer low frequency waves transmitted from the control box in the receptacle to each stimulation pad to provide a body stimulus.

Next, the control box 30 received in the main body receptacle is configured by a box body 31 in the form of a box as shown in FIG. 5, and the box body is partitioned into a battery room 32 and a low frequency wave generating room 33 for receiving a battery and a low frequency wave generator, respectively.

In addition, a connecting terminal 34 is formed on the outer surface of the box body to come into contact with the connected terminal 25 of the main body receptacle when the control box is received by the main body receptacle in order to thereby transfer low frequency waves. An on-off switch 35 is formed on the outer exposed surface for operation and stop by a button manipulation. In addition, a light display unit 36 including an LED is provided on the portion close to the on-off switch in order to display the operation state.

The low frequency wave generator 331 includes a controller for controlling overall operations. When a manipulation signal of the on-off switch 35 is inputted, the low frequency wave generator 331 converts power supplied from the battery into a low frequency wave to then be transmitted to the connecting terminal 34. The low frequency wave transmitted to the connecting terminal is transferred to the first to the fourth stimulation pads 231 to 234 through the connected terminal 25 of the main body receptacle, which comes into contact with the connecting terminal, and through the electric wires 24 connected with the connected terminal in order to thereby provide an electric stimulus to the soles of the feet.

The control box 30 may make a control to generate the low frequency waves when the on-off switch 35 is in the on mode, or to generate the low frequency waves according to a pre-stored pattern in the on mode. At this time, the pattern may be separated into a stimulation period in which the low frequency waves are generated, and a rest period in which the low frequency wave are not generated. The duration of the stimulation period and the rest period may be adjusted, and the output strength of the low frequency wave applied in the stimulation period may be variable. The stimulus may be applied to the left foot and the right foot at the same time or at a time interval. If the stimulus is configured to be applied to the left foot and the right foot at different timings, respectively, sequential low frequency stimulation can be made in order to thereby further improve the stimulation effect by stimulation concentration because the low frequency stimulation can be concentrated on one foot.

That is, the operation of the on-off switch 35 in the on mode may be separated into the first rest period, the first stimulation period, the second rest period, the second stimulation period, the third rest period, and the third stimulation period, and the low frequency waves may be generated for 20 minutes in each stimulation period. The first rest period is configured to have a duration of 60 to 80 minutes such that the stimulus is not applied in order for the user to quickly reach the non-REM sleep after falling asleep. In addition, the time interval of the first rest period may be configured to be different with respect to the left foot and the right foot in order to thereby provide a low frequency stimulus to the left foot and the right foot at different timings. For example, a single pattern may be configured to be 6 hours or 6 hours 20 minutes by configuring the first rest period, the first stimulation period, the second rest period, the second stimulation period, the third rest period, and the third stimulation period to be 60 minutes or 80 minutes, 20 minutes, 120 minutes, 20 minutes, 120 minutes, and 20 minutes, respectively. The repetition of the stimulation and the rest periods is intended to allow the growth hormones to continue to secrete by the stimulation and to promote the secretion of the growth hormone by re-stimulation when the secretion of the growth hormones decreases in order to thereby minimize the sleep disturbance due to the stimulation and in order to thereby prevent the low frequency wave stimulation effect from being lowered because the user's senses are dulled by the continuous stimulation.

In addition, the stimulation may be performed by different low frequency outputs in the first to third stimulation periods. That is, the body stimulation may be performed in various output ranges by applying different low frequency outputs rather than the same low frequency output. For example, a low frequency wave of 50 µA and a low frequency wave of 150 µA may be repeatedly outputted every 30 seconds in the first stimulation period, and a low frequency wave of 75 µA and a low frequency wave of 125 µA may be repeatedly outputted every 30 seconds in the second stimulation period. In addition, a low frequency wave of 100 µA may be outputted in the third stimulation period. If a stimulus is applied by a single output pulse of a low frequency, the user's senses may be dulled, thereby degrading the stimulation effect. Thus, in order to generate the growth hormone continuously, continuous stimulation may be provided by changing the output range, and it was identified whether or not the growth hormone increases according thereto. In addition, the low frequency waves may be outputted in a range that is more than the configured range that does not disturb sleep. It is preferable to output low frequency waves in the range of 50 µA to 200 µA for stimulation because the body stimulation is too weak at 50 µA or less.

As shown in FIGS. 1 to 3, the upper cover 40 of the present invention is formed to be extended from both ends of the top surface of the main body in order to thereby wrap the top of the foot so that the sole of the foot comes into contact with the top surface of the main body.

In addition, the upper cover 40 is preferably provided with a stretchable structure corresponding to various foot sizes. For example, a portion coupled to one side of the main body may be extended to be long, and a portion coupled to the other side thereof may be extended to be short, so that they may be fastened or detached by a buckle or a Velcro tape in order to thereby adjust the size of the inner space into which the foot is inserted by the length adjustment. As shown in the drawing, the first cover portion 41 and the second cover portion 42 may be extended from both sides of the main body to cover the top of the foot, and the space between the extended end portions of the first cover portion and the second cover portion may be adjusted by a tightening member 43.

The tightening member 43 may adjust the space between the first cover portion 41 and the second cover portion 42 in the general shoelace manner. Alternatively, a wire may connect the first cover portion and the second cover portion to be crossed, and then the wire may be wound around a tightening roll to become short or long in order to thereby adjust the space between the ends of the first cover portion 41 and the second cover portion 42.

In addition, an auxiliary cover portion 44 may be further provided between the first cover portion 41 and the second cover portion 42 to rest on the top of the foot in order to thereby prevent the wire of the tightening member from directly pressing the foot through a gap between the first cover portion 41 and the second cover portion 42.

Furthermore, an auxiliary cover band 45, of which ends are coupled to the main body, may be formed in a portion, on which a big toe rests, to maintain the big toe in its position so that the contact between the lower surface of the big toe and the fourth stimulation pad 234 can be maintained in order to thereby provide low frequency stimulation through the fourth stimulation pad.

As shown in FIGS. 2a and 2b, the hooking band 50 is integrally coupled to the rear portion of the upper cover 40, and is formed of an elastic material to be hooked by the heels of the feet.

The hooking band 50 prevents the growth stimulation apparatus from being detached due to twisting and turning while asleep after being worn on the feet in order to thereby provide a low frequency stimulus to important points of the feet while asleep.

The hooking band 50 may include a bottom support 51 that is extended downwards and slantingly from the back of the upper cover 40 to wrap the bottom of the heel, and a back support 52 that is extended backwards from one side of the bottom support to wrap the back of the heel, wherein the bottom support and the back support are formed in the shape of "Y" to be hooked by the heel to then be fixed.

The hooking portion in the Y-shape of the hooking band 50 is intended to allow the hooking band to be hooked by the heel of the foot in a specific position without movement in order to thereby maintain the space therebetween. For example, if the hooking band is positioned only in the back of the heel or only around the ankle, the hooking band 50 may pivot on the joint of the upper cover. Such a change in the hooking position of the hooking band may result in a change in the direction in which a pull force is applied so that the size of a space between the upper cover and the main body, into which the foot is inserted, may vary. That is, when wearing the growth stimulation apparatus, the main body may come into contact with the sole by adjusting the tightening member of the upper cover to conform to the position of the hooking band 50. Afterwards, when the hooking position of the hooking band is changed, the direction in which the hooking band pulls the upper cover also varies so that the space between the upper cover and the main body may increase. If such a space increases, the contact between the sole and the main body is not secured, and thus a transfer rate of the low frequency wave may decrease. Therefore, the hooking band 50 may include the bottom support 51 and the back support 52, which are bifurcated in the shape of Y, in order to thereby minimize a change in the hooking position and in order to thereby improve the contactability between the main body and the sole.

The operation of the growth stimulation apparatus, which has the configuration above, will be described.

The user: puts his/her feet into the space between the main body 20 and the upper cover 40 of the growth stimulation apparatus 10; fixes the hooking band 50 to the heels of the feet; and adjusts the tightening member 43 of the upper cover in order to thereby allow the growth stimulation apparatus to come into contact with the feet.

After wearing the growth stimulation apparatus, the user turns on the on-off switch 35 of the control box 30 and goes to bed. Then, the control box generates low frequency waves according to a configured interval, and applies a stimulus to the soles of the user, which come into contact with the first to the fourth stimulation pads 231 to 234. Even if the wearer twists and turns during the operation time of the growth stimulation apparatus, the growth stimulation apparatus can be prevented from being detached by the tightening member 43 of the upper cover and the hooking band 50.

In addition, when the user takes a walk while wearing the growth stimulation apparatus in which the acupressure protrusions 235 are formed on the first to fourth stimulation pads 231 to 234, the user may walk while lifting up the heels of the feet due to the structure of the growth stimulation apparatus in which a cushion layer to support the heels of the feet is not provided. If the user walks while lifting up the heels, the body weight is concentrated on the front portion of the feet so that the continuous acupressure may be conducted by the acupressure protrusions 235 of the first to the fourth stimulation pads 231 to 234 in order to thereby maximize the stimulation by the acupressure protrusions as well as the stimulation by the low frequency waves.

The accompanying drawings described above are only examples to easily explain the technical concept and subject matter of the present invention, and the scope of the present invention is not limited thereto. In addition, it is obvious to those skilled in the art that various modification and changes can be made based on the embodiments above within the scope of the present invention.

The invention claimed is:

1. A footwear-type growth stimulation apparatus comprising:
a main body configured to have an outer sheath layer on which a contact surface is formed to come into contact with only the front portion of a sole and that has a plurality of stimulation pads formed on the contact surface, and a cushion layer that is integrally coupled with the lower surface of the outer sheath layer to provide a cushion and that has a receptacle formed on one side thereof to have a connected terminal to be connected with a plurality of stimulation pads by electric cables;
a control box configured to be detachably mounted in the receptacle of the main body and configured to have a battery room and a control room that are provided therein to generate low frequency waves by using supplied power and to then transfer the generated low frequency waves to the stimulation pads through the connected terminal of the receptacle, wherein an on-off switch is installed on the outer surface of the control box for operation, and a rest period operation and a stimulation period operation are alternatively performed when the switch is in an on mode,
wherein the operation of the on-off switch in the on mode comprises a first rest period, a first stimulation period, a second rest period, a second stimulation period, a third rest period, and a third stimulation period, and
wherein the low frequency waves are generated for twenty minutes in each stimulation period, a low frequency wave of 50 μA and a low frequency wave of 150 μA are alternatively outputted every 30 seconds in the first stimulation period, a low frequency wave of 75 μA and a low frequency wave of 125 μA are alternatively outputted every thirty seconds in the second stimulation period, and a low frequency wave of 100 μA is outputted in the third stimulation period;
an upper cover configured to be extended from both ends of the top surface of the main body to wrap the top of a foot; and
a hooking band configured to be integrally coupled to the upper cover to be extended backwards and configured to be formed of an elastic material to be hooked by the heel of the foot.

2. The apparatus according to claim 1, wherein the stimulation pads are formed on four portions of the outer sheath layer,
wherein a stimulation pad formed on a first portion of the four portions comes into contact with the middle of the front portion of the sole corresponding to the Bubbling Spring, a stimulation pad formed on a second portion of the four portions comes into contact with the sole where a big toe is joined in the front portion of the sole, a stimulation pad formed on a third portion of the four portions comes into contact with the sole where a little toe is joined in the front portion of the sole, and a stimulation pad formed on a fourth portion of the four portions comes into contact with a lower surface of the big toe, and wherein acupressure protrusions are formed on the stimulation pads to provide acupressure to the sole.

3. The apparatus according to claim 1, wherein the upper cover comprises:
- a first cover portion and a second cover portion, which are configured to be extended from both sides of the main body; and
- a tightening member configured to connect the first cover portion and the second cover portion in order to thereby adjust a space between the upper cover and the main body.

4. The apparatus according to claim 1, wherein the hooking band comprises:
- a bottom support configured to be extended downwards and slantingly from the back of the upper cover to wrap the bottom of the heel; and
- a back support configured to be extended backwards from one side of the bottom support to wrap the back of the heel.

* * * * *